United States Patent [19]

Pray

[11] 3,938,986

[45] Feb. 17, 1976

[54] HERBICIDE

[75] Inventor: Blaine O. Pray, Ponce, P.R.

[73] Assignee: PPG Industries, Inc., Pittsburgh, Pa.

[22] Filed: July 28, 1970

[21] Appl. No.: 59,004

Related U.S. Application Data

[63] Continuation-in-part of Ser. No. 807,934, March 17, 1969, abandoned, which is a continuation-in-part of Ser. No. 580,891, Sept. 21, 1966, abandoned, and a continuation-in-part of Ser. No. 599,699, Dec. 7, 1966, abandoned, and a continuation-in-part of Ser. No. 631,593, April 18, 1967, abandoned.

[52] U.S. Cl. ........................ 111/111; 71/94; 71/98; 71/100; 71/105; 71/106
[51] Int. Cl.² ............................................ A01N 9/20
[58] Field of Search ............................. 71/111, 106

[56] References Cited
UNITED STATES PATENTS

| | | | |
|---|---|---|---|
| 2,776,196 | 1/1957 | Gysin et al. | 71/111 X |
| 2,776,197 | 1/1957 | Gysin et al. | 71/111 X |
| 2,812,247 | 11/1957 | Gysin et al. | 71/111 X |

OTHER PUBLICATIONS

Canode et al., Weeds, Vol. 10, No. 3, pp. 216–219 (1962).
Agronomy Abstracts, 1965, p. 85.

*Primary Examiner*—Glennon H. Hollrah
*Attorney, Agent, or Firm*—Mark Levin; George D. Morris

[57] ABSTRACT

Herbicidally active alkyl N-phenylcarbamates are employed in combination with phenyl esters of N-alkylcarbamic acid or N,N-dialkylcarbamic acid. For example, a herbicidally active isopropyl N-phenylcarbamate is formulated in admixture with a phenyl N-methylcarbamate. The presence of the N-alkylcarbamate enhances the effectiveness of the N-phenylcarbamate as a herbicide by extending its soil persistence, increasing its herbicidal activity and/or altering its spectrum of practical herbicidal activity.

7 Claims, No Drawings

HERBICIDE

RELATED APPLICATIONS

This application is a continuation-in-part of U.S. application Ser. No. 807,934, filed Mar. 17, 1969, now abandoned, which is:
1. a continuation-in-part of U.S. application Ser. No. 580,891, filed Sept. 21, 1966, now abandoned;
2. a continuation-in-part of U.S. application Ser. No. 599,699, filed Dec. 7, 1966 now abandoned; and
3. a continuation-in-part of U.S. application Ser. No. 631,593, filed Apr. 18, 1967 now abandoned, which is a continuation-in-part of said U.S. application Ser. No. 580,891 and a continuation-in-part of said U.S. application Ser. No. 599,699.

This invention relates to the use of herbicidally active alkyl N-phenylcarbamates, as defined hereinafter, in combination with the phenyl esters of N-alkyl- and N,N-dialkylcarbamic acids. It has been found that the herbicidal effectiveness of the alkyl N-phenylcarbamates is enhanced by formulating or applying them in combination with the phenyl N-alkylcarbamates. Certain embodiments of this invention are directed to suitable formulations including both alkyl N-phenylcarbamate and phenyl N-alkylcarbamate.

The herbicidally active N-phenylcarbamates of this invention belong to the class which includes both substituted and non-substituted alkyl esters of either substituted or non-substituted N-phenylcarbamic acid. The alkyl ester constituent is lower alkyl and usually contains 8 or fewer carbon atoms although it may in rare instances contain 20 or more carbon atoms. The alkyl chain may be branched and it may be substituted at any position with a halogen, preferably chlorine, but including fluorine, bromine and iodine or nitrogen. Sometimes the alkyl ester has more than one substituent. The acyl oxygen may be substituted with sulfur. Permissible substituents which may be placed on the phenyl ring include alkyl, haloalkyl, alkylamino, dialkylamino, alkoxy, alkoxymethyl, alkenyl, nitro, amino, acetamino, cyano, isocyanato and halo. The term "halo" as used herein includes chloro, iodo, bromo and fluoro. The term "halogen" includes all four of the halogens. In general, of the constituents which contain carbon atoms, those which contain 1 or 2 carbon atoms are most common and generally most active. Such substituents may contain up to 4 or more, rarely more than 6, carbon atoms. Of course, the dialkyl substituents, such as the dialkylamino substituents generally contain twice these numbers, i.e., usually 2 through 4, rarely more than 12 carbon atoms. Chlorine is the most useful halogen substituent. The substituents may be present in any position of the ring. More than one substituent may be present.

It is well known that many N-phenylcarbamates of the aforedescribed class possess significant herbicidal activity. Although only a few of these carbamates, notably isopropyl N-phenylcarbamate, isopropyl N-(3-chlorophenyl)-carbamate, methyl N-(3,4-dichlorophenyl)carbamate, 4-chloro-2-butynyl N-(3-chlorophenyl)carbamate and 2-chloroethyl N-(3-chlorophenyl)carbamate have enjoyed wide commercial acceptance, many other members of this class of carbamates are potentially useful. Often the herbicidal activity of a particular alkyl N-phenylcarbamate is highly specific to certain plants or families of plants.

Examples of specific carbamates included in the term "herbicidally active alkyl N-phenylcarbamate" are: sec-butyl N-(3-chlorophenyl)carbamate, isopropyl N-(3-chlorophenyl)carbamate, butyl N-phenylcarbamate, isopropyl N-(3-chloro-6-methoxyphenyl)carbamate, isopropyl N-(3-methylphenyl)carbamate, isopropyl N-(2,5-dichlorophenyl)carbamate, isopropyl N-(3-chloro-6-methylphenyl)carbamate, isopropyl N-phenylthionocarbamate, 2-chloroethyl N-(3-chlorophenyl)-carbamate, n-butyl N-phenylcarbamate, isopropyl N-(2-chlorophenyl)carbamate, isopropyl N-(2-methoxyphenyl)carbamate, isopropyl N-(3,4-dichlorophenyl)carbamate, isopropyl N-(2,4-dichlorophenyl)-carbamate, 2-ethylhexyl N-phenylcarbamate, n-propyl N-phenylcarbamate, lauryl N-phenylcarbamate, isopropyl N-phenylcarbamate, isopropyl N-(2-pyridyl)-carbamate, isopropyl N-(4-chlorophenyl)carbamate, isopropyl N-(3,5-dichlorophenyl)carbamate, ethyl N-phenylcarbamate, isopropyl N-(3-acetophenyl)carbamate, 3-chloropropyl N-phenylcarbamate, isopropyl N-(3-trifluoromethylphenyl)carbamate, and isopropyl N-(2-methylphenyl)carbamate.

A subclass of particular interest to the instant invention consists of isopropyl N-phenylcarbamate and the isopropyl N-(chlorophenyl)carbamates, e.g., isopropyl N-(3-chlorophenyl)carbamate, isopropyl N-(3,4-dichlorophenyl)-carbamate, isopropyl N-(2,5-dichlorophenyl)carbamate, isopropyl N-(2-chlorophenyl)carbamate, isopropyl N-(2,4-dichlorophenyl)-carbamate, isopropyl N-(3,5-dichlorophenyl)-carbamate and isopropyl N-(4-chlorophenyl)carbamate.

Both isopropyl N-phenylcarbamate and isopropyl N-(3-chlorophenyl)carbamate have long been recognized as good pre-emergence herbicides for the control of various weeds. As is the case with many other herbicides, these carbamates have been found to decompose or become deactivated within a relatively short time, e.g., within about 2 to 4 weeks, rarely more than about 6 weeks after being applied to the soil. It has further been observed that when these carbamates are repeatedly applied to the same soil area, the period of herbicidal activity tends to become shorter with each application. Accordingly, high application rates of these carbamates have been required to maintain a desired concentration thereof in the soil at a prescribed period after application.

According to the present invention, it has been found that the soil persistence of the herbicidally active alkyl N-phenylcarbamates is significantly extended by applying the alkyl N-phenylcarbamate to the soil along with an effective amount of a phenyl (including substituted phenyl) N-alkylcarbamate. By "effective amount" is meant an amount which results in a measurable increase in the "soil life" of the alkyl N-phenylcarbamate. The soil life of a herbicide is readily determined by simple test procedures.

According to one such procedure, a quantity of soil is divided into portions. A pre-determined amount of herbicide, usually a considerable excess over the amount known to be herbicidal, is mixed with one portion of the soil. At prescribed intervals, e.g., each day or each week, samples are taken from both the untreated and the treated soil. Seeds, e.g., rye grass seeds, are planted in each sample. When the seeds planted in the treated soil grow normally as compared to seeds planted in the untreated soil, the soil life of the herbicide is considered to be exhausted, even though analysis of the soil might show the presence of some herbicide. The soil life of a herbicide as measured by this test will vary in duration depending, among other things, on the soil type and species of seeds selected for the test. Nevertheless, the test is useful to determine whether the presence of a given amount of the claimed phenyl N-alkylcarbamate results in an extension of the soil life of an alkyl N-phenylcarbamate.

In addition to extending the soil life of the herbicidally active alkyl N-phenylcarbamate, the presence of the phenyl N-alkylcarbamate often enhances the herbicidal effectiveness of the alkyl N-phenylcarbamate against a specific weed or class of weeds. The combined carbamates may possess a pattern of selectivity not possessed by the alkyl N-phenylcarbamate alone or it may merely demonstrate increased activity. In any event, the combined carbamates often selectively inhibit in specific crops the growth of specific weeds not so inhibited by the herbicidally active alkyl N-phenylcarbamate alone. This result is observed at application rates of the alkyl N-phenylcarbamate below those traditionally employed even though the phenyl N-alkylcarbamates of this invention do not generally possess any commercially significant herbicidal value.

The phenyl N-alkylcarbamates of this invention whose alkyl groups are lower alkyl include both substituted and non-substituted phenyl esters of the N-alkylcarbamic acids and the N,N-dialkylcarbamic acids wherein the alkyl groups of these acids independently contain from 1 through 4 carbon atoms. Either the acyl or the ester or both the acyl and the ester oxygen atoms may be substituted with sulfur. The rings of the phenyl nucleus may contain nitrogen, sulfur and/or oxygen as hereto atoms.

Permissible substituent groups for the nucleus include alkyl with up through 4 carbon atoms, alkynyl with up through 4 carbon atoms, dialkylamino in which each of the alkyl constituents contains up through 4 carbon atoms, alkoxy with up through 4 carbon atoms, alkenyl with up through 4 carbon atoms, alkylmercapto with up to 4 carbon atoms, nitro, amino, acetamino, cyano, isocyanato and halo (including chloro, iodo, bromo and fluoro). In general, of the substituents which contain hydrocarbon constituents, those in which the hydrocarbon constituents have 1 or 2 carbon atoms are preferred. Chlorine is the preferred halogen substituent. The substituents may be present in any position in the nucleus. More than one substituent may be present.

Among the phenyl N-methylcarbamates useful in the practice of this invention are: phenyl N-methylcarbamate, 2-tolyl N-methylcarbamate, 3-tolyl N-methylcarbamate, 4-tolyl N-methylcarbamate, 3-ethylphenyl N-methylcarbamate, 2-isopropylphenyl N-methylcarbamate, 3-isopropylphenyl N-methylcarbamate, 4-isopropylphenyl N-methylcarbamate, 2-tert-butylphenyl N-methylcarbamate, 3-tert-butylphenyl N-methylcarbamate, 4-tert-butylphenyl N-methylcarbamate, 2-nitrophenyl N-methylcarbamate, 3-nitrophenyl N-methylcarbamate, 4-nitrophenyl N-methylcarbamate, 2-chlorophenyl N-methylcarbamate, 3-chlorophenyl N-methylcarbamate, 4-chlorophenyl N-methylcarbamate, 2-cyclohexylphenyl N-methylcarbamate, 3,5-dimethylphenyl N-methylcarbamate, 3-dimethylaminophenyl N-methylcarbamate, 4-dimethylaminophenyl N-methylcarbamate, 3-dimethylaminophenylmethiodide N-methylcarbamate, 2-methyl-5-isopropylphenyl N-methylcarbamate, 3-methyl-5-isopropylphenyl N-methylcarbamate, 5-methyl-2-isopropylphenyl N-methylcarbamate, 2,3,5-trimethylphenyl N-methylcarbamate, 2,4-di-tert-butylphenyl N-methylcarbamate, 2,4-dichlorophenyl N-methylcarbamate, 2,4-dinitrophenyl N-methylcarbamate, 2-methyl-4,6-dinitrophenyl N-methylcarbamate, 2,6-dimethoxy-3,5-dinitrophenyl N-methylcarbamate, 2,4,5-trichlorophenyl N-methylcarbamate, 2,4,6-trichlorophenyl N-methylcarbamate, 4-dimethylamino-3,5-dimethylphenyl N-methylcarbamate, 3,5-dimethyl-4-methylthiophenyl N-methylcarbamate, 2-isopropoxyphenyl N-methylcarbamate, 4-dimethylamino-3-tolyl N-methylcarbamate, 3-sec-butylphenyl N-methylcarbamate, 2-chloro-3-isopropylphenyl N-methylcarbamate and 3-methyl-4-methylthiophenyl N-methylcarbamate.

Among the phenyl N,N-dimethylcarbamates useful in the practice of this invention are: phenyl N,N-dimethylcarbamate, 5,5-dimethyldihydroresorcinol N,N-dimethylcarbamate and 6-(2-n-propyl-4-pyridinyl) N,N-dimethylcarbamate.

The corresponding esters of N-ethylcarbamic acid, N,N-diethylcarbamic acid, the N-propylcarbamic acids, the N,N-dipropylcarbamic acids, the N-butylcarbamic acids and the N,N-dibutylcarbamic acids are often useful. For example, compounds such as phenyl N-ethylcarbamate, phenyl N-propylcarbamate, 2-chlorophenyl N,N-dipropylcarbamate, phenyl N,N-di-n-propylthiocarbamate, 4-dimethylamino-3-isopropylphenyl N-ethylcarbamate, 4-dimethylamino-3,5-dimethylphenyl N-methylcarbamate and 3-chlorophenyl N-tert-butylcarbamate are within contemplation. The two alkyl groups attached to the nitrogen atom of the N,N-dialkylcarbamates may be the same or they may be different.

In general, the N-methylcarbamates and the N,N-dimethylcarbamates represent a preferred class.

The benefits of the present invention may be obtained by treating either the soil or the vegetation growing in the soil with separate formulations of the carbamates. For example, a liquid formulation of a phenyl N-methylcarbamate may be sprayed on the soil. A formulation containing an alkyl N-phenylcarbamate is applied to the same area within a short time, e.g., within a few days, usually within about 36 hours after application of the phenyl N-methylcarbamate. The carbamates may then be incorporated into the soil by disking or watering, if desired. Ordinarily, it is more convenient to formulate an effective amount of the phenyl N-alkylcarbamate in a formulation with the herbicidal alkyl N-phenylcarbamate. Many of the formulations presently employed by the art for the application of alkyl N-phenylcarbamates to the soil are readily adapted to include an effective amount of a phenyl N-alkylcarbamate.

What constitutes an "effective amount" of the phenyl N-alkylcarbamate in a formulation depends upon the specific alkyl N-phenylcarbamate employed, the specific phenyl N-alkylcarbamate employed, the specific formulation in which said phenyl N-alkylcarbamate and alkyl N-phenylcarbamate are incorporated and the soil conditions where the formulation is to be applied. The useful ratio of isopropyl N-phenylcarbamate to phenyl N-alkylcarbamate, for example, is highly variable. Between about 10 parts and 1 part of isopropyl N-phenylcarbamate may be mixed with about 1 to about 10 parts of the phenyl N-alkylcarbamate by weight. For reasons of economy, among other considerations, typical formulations contain between about 1 to about 5 parts of isopropyl N-phenylcarbamate with about 1 part by weight of the phenyl N-alkylcarbamate. Similar porportions are generally useful when other alkyl N-phenylcarbamates, notably isopropyl N-(3-chlorophenyl)carbamate is substituted for isopropyl N-phenylcarbamate in the formulation.

The quantity of alkyl N-phenylcarbamate required to be applied to the soil with the formulations of this invention for weed control is usually reduced over the quantities required when the alkyl N-phenylcarbamate is applied alone. Application rates of the formulations of this invention vary with the ratios of the alkyl N-phenylcarbamate to the phenyl N-alkylcarbamate in the mixture, the method of application, the result to be achieved and the specific weeds to be combatted, among other factors.

Effective compositions may be prepared containing the mixed carbamates in amounts between about 1 and about 90 percent by weight. These compositions may then be diluted and employed in concentrations, i.e., weight percent carbamate, as low as 1 percent or less by weight. For most applications, the compositions of this invention will be applied to advantage in concentrations of about ½ to about 10 percent by weight in conjunction with fluid carriers, as solutions, emulsions, or dispersions of wettable powders. They may also be applied with solid carriers or diluents or in granular formulations.

The extension of the soil persistence of the alkyl N-phenylcarbamates by the phenyl N-alkylcarbamates of this invention is illustrated by the following examples.

EXAMPLE I

Sandy loam soil is taken from an area north of and in the vicinity of Akron, Ohio and is screened to remove stones and other large objects. Seven hundred fifty (750) gram samples of soil are then placed in 12 × 20 inches polyethylene bags. A solution of each test compound is prepared by placing a 0.396 gram portion of the test compound in a 100 milliliter volumetric flask, dissolving the portion in acetone and diluting to volume with acetone and water such that a 1 milliliter aliquot when blended with a 750 gram soil sample yields a concentration of 2 pounds of test compound per acre-inch of soil. Enough acetone to keep the test compound in solution is maintained. For each 2 pounds of test compound per acre-inch of soil, a 1 milliliter aliquot is taken from the appropriate flask and atomized onto the soil in the plastic bag, which soil has been spread out to form a ¼ inch thick layer. Air is blown over the soil for about one minute to evaporate a portion of the acetone present. The soil is then blended by shaking the bag for 2 minutes, sealed with a rubber band and stored. Periodically a small soil sample (30 to 50 grams) is taken from each of the bags and placed in a 6 ounce plastic cup to which about 3 milliliters of water has been added. Ten rye grass (*Lolium multiflorum*) seeds are planted in each cup ⅛ inch below the soil surface. The cups are then sealed with a piece of polyethylene held in place with a rubber band to prevent moisture loss. After a growing period of 7 days, the rye grass plants are cut off at the soil line and weighed. The amount of growth is then tabulated with the amount of test compound in the soil. The results are shown in Table 1 and 1A.

TABLE 1A

GRAMS OF RYE GRASS TOP GROWTH PLANTED ON VARIOUS DAYS AFTER TREATMENT

| TEST COMPOUND | NUMBER OF DAYS | | | | | | | | |
|---|---|---|---|---|---|---|---|---|---|
| | 2 | 9 | 16 | 23 | 32 | 43 | 53 | 63 | 79 |
| Control | 0.050 | 0.073 | 0.068 | 0.096 | 0.075 | 0.098 | 0.103 | 0.073 | 0.065 |
| Isopropyl N-(3-chlorophenyl)carbamate (6 lb./acre-in.) | 0.000 | 0.000 | 0.000 | 0.000 | 0.000 | 0.000 | 0.000 | 0.000 | 0.000 |
| Isopropyl N-(3-chlorophenyl)carbamate (6 lb./acre-in.) 4-Chlorophenyl N-methylcarbamate (1½ lb./acre-in.) | 0.000 | 0.000 | 0.000 | 0.000 | 0.000 | 0.000 | 0.000 | 0.000 | 0.000 |
| 4-Chlorophenyl N-methylcarbamate (7½ lb./acre-in.) | 0.060 | 0.078 | 0.068 | 0.083 | 0.087 | 0.086 | 0.076 | 0.077 | 0.073 |
| | 92 | 109 | 123 | 136 | 155 | 178 | | | |
| Control | 0.065 | 0.059 | 0.093 | 0.113 | 0.084 | 0.073 | | | |
| Isopropyl N-(3-chlorophenyl)carbamate (6 lb./acre-in.) | 0.000 | 0.000 | 0.030 | 0.047 | 0.057 | 0.070 | | | |
| Isopropyl N-(3-chlorophenyl)carbamate (6lb./acre-in.) 4-Chlorophenyl N-methylcarbamate (1½ lb./acre-in.) | 0.000 | 0.000 | 0.000 | 0.004 | 0.000 | 0.000 | | | |
| 4-Chlorophenyl N-methylcarbamate (7½ lb./acre-in.) | 0.054 | 0.047 | — | — | — | — | | | |

TABLE 1

GRAMS OF RYE GRASS TOP GROWTH PLANTED ON VARIOUS DAYS AFTER TREATMENT

| TEST COMPOUND | NUMBER OF DAYS | | | | | | | | |
|---|---|---|---|---|---|---|---|---|---|
| | 1 | 8 | 15 | 22 | 33 | 40 | 50 | 60 | 76 |
| Control | 0.060 | 0.095 | 0.050 | 0.104 | 0.096 | 0.104 | 0.098 | 0.093 | 0.098 |
| Isopropyl N-(3-chlorophenyl)carbamate (10 lb./acre-in.) | 0.000 | 0.000 | 0.000 | 0.000 | 0.000 | 0.000 | 0.000 | 0.000 | 0.000 |
| Isopropyl N-(3-chlorophenyl)carbamate (8 lb./acre-in.) | 0.000 | 0.000 | 0.000 | 0.000 | 0.000 | 0.000 | 0.000 | 0.000 | 0.000 |
| Isopropyl N-phenylcarbamate (10 lb./acre-in.) | 0.000 | 0.000 | 0.000 | 0.000 | 0.000 | 0.000 | 0.005 | 0.032 | 0.053 |
| Isopropyl N-phenylcarbamate (8 lb./acre-in.) | 0.000 | 0.000 | 0.000 | 0.000 | 0.000 | 0.000 | 0.000 | 0.011 | 0.078 |
| Isopropyl N-(3-chlorophenyl)carbamate (8 lb./acre-in.) 4-Chlorophenyl N-methylcarbamate (2 lb./acre-in.) | 0.000 | 0.000 | 0.000 | 0.000 | 0.000 | 0.000 | 0.000 | 0.000 | 0.000 |
| Isopropyl N-(3-chlorophenyl)carbamate (8 lb./acre-in.) 3-Chlorophenyl N-methylcarbamate (2 lb./acre-in.) | 0.000 | 0.000 | 0.000 | 0.000 | 0.000 | 0.000 | 0.000 | 0.000 | 0.000 |
| Isopropyl N-phenylcarbamate (8 lb./acre-in.) 4-Chlorophenyl N-methylcarbamate (2 lb./acre-in.) | 0.000 | 0.000 | 0.000 | 0.000 | 0.000 | 0.000 | 0.005 | 0.000 | 0.000 |
| Isopropyl N-phenylcarbamate (8 lb./acre-in.) 3-Chlorophenyl N-methylcarbamate (2 lb./acre-in.) | 0.000 | 0.000 | 0.000 | 0.000 | 0.000 | 0.000 | 0.000 | 0.000 | 0.000 |
| 4-Chlorophenyl N-methylcarbamate (10 lb./acre-in.) | 0.070 | 0.050 | 0.050 | 0.056 | 0.050 | 0.052 | 0.093 | 0.069 | 0.071 |
| 4-Chlorophenyl N-methylcarbamate (2 lb./acre-in.) | 0.065 | 0.060 | 0.050 | 0.076 | 0.060 | 0.098 | 0.091 | 0.089 | 0.082 |

TABLE 1-continued

| TEST COMPOUND | GRAMS OF RYE GRASS TOP GROWTH PLANTED ON VARIOUS DAYS AFTER TREATMENT | | | | | | | | |
|---|---|---|---|---|---|---|---|---|---|
| | NUMBER OF DAYS | | | | | | | | |
| | 1 | 8 | 15 | 22 | 33 | 40 | 50 | 60 | 76 |
| 3-Chlorophenyl N-methylcarbamate (10 lb./acre-in.) | 0.040 | 0.045 | 0.063 | 0.084 | 0.098 | 0.103 | 0.099 | 0.074 | 0.094 |
| 3-Chlorophenyl N-methylcarbamate (2 lb./acre-in.) | 0.070 | 0.060 | 0.070 | 0.092 | 0.089 | 0.107 | 0.094 | 0.092 | 0.079 |
| | | | | 89 | 106 | 120 | 133 | 152 | 175 |
| Control | | | | 0.089 | 0.074 | 0.078 | 0.108 | 0.105 | 0.093 |
| Isopropyl N-(3-chlorophenyl)carbamate (10 lb./acre-in.) | | | | 0.005 | 0.007 | 0.000 | 0.014 | 0.032 | 0.049 |
| Isopropyl N-(3-chlorophenyl)carbamate (8 lb./acre-in.) | | | | 0.000 | 0.009 | 0.007 | 0.042 | 0.047 | 0.058 |
| Isopropyl N-phenylcarbamate (10 lb./acre-in.) | | | | 0.091 | 0.090 | 0.093 | 0.091 | — | — |
| Isopropyl N-phenylcarbamate (8 lb./acre-in.) | | | | 0.084 | 0.050 | 0.083 | 0.103 | — | — |
| Isopropyl N-(3-chlorophenyl)carbamate (8 lb./acre-in.) 4-Chlorophenyl N-methylcarbamate (2 lb./acre-in.) | | | | 0.000 | 0.000 | 0.000 | 0.000 | 0.000 | 0.000 |
| Isopropyl N-(3-chlorophenyl)carbamate (8 lb./acre-in.) 3-Chlorophenyl N-methylcarbamate (2 lb./acre-in.) | | | | 0.000 | 0.000 | 0.000 | 0.004 | 0.041 | 0.050 |
| Isopropyl N-phenylcarbamate (8 lb./acre-in.) 4-Chlorophenyl N-methylcarbamate (2 lb./acre-in.) | | | | 0.000 | 0.000 | 0.023 | 0.031 | 0.077 | 0.080 |
| Isopropyl N-phenylcarbamate (8 lb./acre-in.) 3-Chlorophenyl N-methylcarbamate (2 lb./acre-in.) | | | | 0.015 | 0.012 | 0.032 | 0.108 | 0.084 | 0.063 |
| 4-Chlorophenyl N-methylcarbamate (10 lb./acre-in.) | | | | 0.052 | 0.065 | — | — | — | — |
| 4-Chlorophenyl N-methylcarbamate (2 lb./acre-in.) | | | | 0.091 | 0.051 | — | — | — | — |
| 3-Chlorophenyl N-methylcarbamate (10 lb./acre-in.) | | | | 0.075 | 0.061 | — | — | — | — |
| 3-Chlorophenyl N-methylcarbamate (2 lb./acre-in.) | | | | 0.082 | 0.052 | — | — | — | — |

EXAMPLE II

Top soil is taken from an area south of and in the vicinity of Barberton, Ohio and is screened to remove stones and other large objects. One thousand (1000) gram samples of soil are then placed in 12 × 20 inch polyethylene bags. A solution of isopropyl N-(3-chlorophenyl)carbamate is prepared by placing a 0.210 gram portion of this compound in a 100 milliliter volumetric flask, dissolving the portion in acetone and diluting to volume with acetone and water. A solution of each of the other test compounds is prepared by placing a 0.050 gram portion of the test compound in a 100 milliliter volumetric flask, dissolving the portion in acetone and diluting to volume with acetone and water. In each case, enough acetone is maintained to keep the compound in solution. A 10 milliliter aliquot of the isopropyl N-(3-chlorophenyl)carbamate solution when mixed with 1000 grams of soil is equivalent to 8 pounds of the compound per acre-inch of soil. A 10 milliliter aliquot of each of the other solutions when mixed with 1000 grams of soil is equivalent to 2 pounds per acre-inch of soil. Ten milliliter aliquots are taken from the appropriate flasks and atomized onto the soil in the plastic bags, which soil has been spread out to form a ¼ inch thick layer. The soil is then blended by shaking the bag for 2 minutes. The bags are then sealed with a rubber band and stored. Periodically, a small soil sample (30 to 50 grams) is taken from each of the bags and placed in a 6 ounce plastic cup to which about 3 milliliters of water has been added. Ten (10) rye grass (*Lolium multiflorum*) seeds are planted in each cup ⅛ inch below the soil surface. The cups are then sealed with a piece of polyethylene held in place with a rubber band to prevent moisture loss. After a growing period of 7 days, the rye grass plants are cut off at the soil line and weighed. The amount of growth is then tabulated with the amount of test compound in the soil. The results are shown in Table 2.

TABLE 2

| TEST COMPOUND | GRAMS OF RYE GRASS TOP GROWTH PLANTED ON VARIOUS DAYS AFTER TREATMENT | | | | | | | | |
|---|---|---|---|---|---|---|---|---|---|
| | NUMBER OF DAYS | | | | | | | | |
| | 0 | 4 | 7 | 11 | 14 | 18 | 21 | 25 | 28 |
| Control | 0.060 | 0.086 | 0.035 | 0.064 | 0.086 | 0.090 | 0.105 | 0.097 | 0.120 |
| Isopropyl N-(3-chlorophenyl)carbamate (8 lb./acre-in.) | 0.000 | 0.000 | 0.000 | 0.000 | 0.014 | 0.093 | 0.105 | 0.105 | 0.058 |
| Isopropyl N-(3-chlorophenyl)carbamate (8 lb./acre-in.) Phenyl N-methylcarbamate | 0.000 | 0.000 | 0.000 | 0.000 | 0.000 | 0.000 | 0.000 | 0.000 | 0.000 |
| Isopropyl N-(3-chlorophenyl)carbamate (8 lb./acre-in.) 4-Chlorophenyl N-methylcarbamate (2 lb./acre-in.) | 0.000 | 0.000 | 0.000 | 0.000 | 0.000 | 0.000 | 0.000 | 0.000 | 0.000 |
| Isopropyl N-(3-chlorophenyl)carbamate (8 lb./acre-in.) 3-Chlorophenyl N-methylcarbamate (2 lb./acre-in.) | 0.000 | 0.000 | 0.000 | 0.000 | 0.000 | 0.000 | 0.000 | 0.000 | 0.000 |
| Isopropyl N-(3-chlorophenyl)carbamate (8 lb./acre-in.) 2-Chlorophenyl N-methylcarbamate (2 lb./acre-in.) | 0.000 | 0.000 | 0.000 | 0.000 | 0.000 | 0.000 | 0.000 | 0.000 | 0.000 |
| Isopropyl N-(3-chlorophenyl)carbamate (8 lb./acre-in.) 3-Methyl-4-methylthiophenyl N-methylcarbamate (2 lb./acre-in.) | 0.000 | 0.000 | 0.000 | 0.000 | 0.000 | 0.000 | 0.000 | 0.000 | 0.000 |
| | 32 | 35 | 39 | 42 | 46 | 49 | 53 | 56 | 61 |
| Control | 0.070 | 0.108 | 0.090 | 0.090 | 0.078 | 0.105 | 0.102 | 0.146 | 0.100 |
| Isopropyl N-(3-chlorophenyl)carbamate (8 lb./acre-in.) | 0.090 | 0.099 | 0.085 | 0.085 | 0.105 | 0.110 | | | |
| Isopropyl N-(3-chlorophenyl)carbamate (8 lb./acre-in.) Phenyl N-methylcarbamate | 0.003 | 0.011 | 0.070 | 0.060 | 0.099 | 0.110 | | | |
| Isopropyl N-(3-chlorophenyl)carbamate (8 lb./acre-in.) 4-Chlorophenyl N-methylcarbamate (2 lb./acre-in.) | 0.004 | 0.000 | 0.000 | 0.000 | 0.002 | 0.000 | 0.003 | 0.006 | 0.012 |
| Isopropyl N-(3-chlorophenyl)carbamate (8 lb./acre-in.) 3-Chlorophenyl N-methylcarbamate (2 lb./acre-in.) | 0.000 | 0.000 | 0.000 | 0.000 | 0.005 | 0.000 | 0.023 | 0.037 | 0.039 |
| Isopropyl N-(3-chlorophenyl)carbamate (8 lb./acre-in.) 2-Chlorophenyl N-methylcarbamate (2 lb./acre-in.) | 0.000 | 0.030 | 0.115 | 0.088 | 0.079 | | | | |

TABLE 2-continued

| TEST COMPOUND | GRAMS OF RYE GRASS TOP GROWTH PLANTED ON VARIOUS DAYS AFTER TREATMENT | | | | | | | | |
|---|---|---|---|---|---|---|---|---|---|
| | NUMBER OF DAYS | | | | | | | | |
| | 32 | 35 | 39 | 42 | 46 | 49 | 53 | 56 | 61 |
| Isopropyl N-(3-chlorophenyl)carbamate (8 lb./acre-in.) 3-Methyl-4-methylthiophenyl N-methylcarbamate (2 lb./acre-in.) | 0.000 | 0.000 | 0.015 | 0.025 | 0.067 | 0.047 | 0.080 | | |

| | 63 | 67 | 70 |
|---|---|---|---|
| Control | 0.099 | 0.060 | 0.106 |
| Isopropyl N-(3-chlorophenyl)carbamate (8 lb./acre-in.) Isopropyl N-(3-chlorophenyl)carbamate (8 lb./acre-in.) Phenyl N-methylcarbamate | | | |
| Isopropyl N-(3-chlorophenyl)carbamate (8 lb./acre-in.) 4-Chlorophenyl N-methylcarbamate (2 lb./acre-in.) | 0.035 | 0.075 | 0.109 |
| Isopropyl N-(3-chlorophenyl)carbamate (8 lb./acre-in.) 3-Chlorophenyl N-methylcarbamate (2 lb./acre-in.) | 0.071 | 0.103 | 0.104 |
| Isopropyl N-(3-chlorophenyl)carbamate (8 lb./acre-in.) 2-Chlorophenyl N-methylcarbamate (2 lb./acre-in.) | | | |
| Isopropyl N-(3-chlorophenyl)carbamate (8 lb./acre-in.) 3-Methyl-4-methylthiophenyl N-methylcarbamate (2 lb./acre-in.) | | | |

EXAMPLE III

The procedure of Example II is followed, except that only 8 milliliter aliquots of test compounds other than isopropyl N-(3-chlorophenyl)carbamate are atomized onto the soil. This corresponds to a concentration of 1.6 pounds of test compound per acre-inch of soil. The results are shown in Table 3.

TABLE 3

| TEST COMPOUND | GRAMS OF RYE GRASS TOP GROWTH PLANTED ON VARIOUS DAYS AFTER TREATMENT | | | | | | | |
|---|---|---|---|---|---|---|---|---|
| | NUMBER OF DAYS | | | | | | | |
| | 1 | 5 | 8 | 12 | 15 | 19 | 22 | 27 |
| Control | 0.100 | 0.080 | 0.085 | 0.095 | 0.099 | 0.080 | 0.080 | 0.102 |
| Isopropyl N-(3-chlorophenyl) N-methylcarbamate (8 lb./acre-in.) | 0.000 | 0.000 | 0.000 | 0.000 | 0.000 | 0.000 | 0.000 | 0.003 |
| Isopropyl N-(3-chlorophenyl) N-methylcarbamate (8 lb./acre-in.) 4-Chlorophenyl N-methylcarbamate (1.6 lb./acre-in.) | 0.000 | 0.000 | 0.000 | 0.000 | 0.000 | 0.000 | 0.000 | 0.000 |
| Isopropyl N-(3-chlorophenyl) N-methylcarbamate (8 lb./acre-in.) 3-Chlorophenyl N-methylcarbamate (1.6 lb./acre-in.) | 0.000 | 0.000 | 0.000 | 0.000 | 0.000 | 0.000 | 0.000 | 0.000 |
| Isopropyl N-(3-chlorophenyl) N-methylcarbamate (8 lb./acre-in.) 2,4-Dichlorophenyl N-methylcarbamate (1.6 lb./acre-in.) | 0.000 | 0.000 | 0.000 | 0.000 | 0.000 | 0.000 | 0.000 | 0.000 |
| Isopropyl N-(3-chlorophenyl) N-methylcarbamate (8 lb./acre-in.) 2,4-Dinitro-6-sec-butylphenyl N-methylcarbamate (1.6 lb./acre-in.) | 0.000 | 0.000 | 0.000 | 0.000 | 0.000 | 0.000 | 0.000 | 0.000 |
| Isopropyl N-(3-chlorophenyl) N-methylcarbamate (8 lb./acre-in.) S-m-propyl N,N-di-n-propylthiolcarbamate (1.6 lb./acre-in.) | 0.000 | 0.000 | 0.000 | 0.000 | 0.000 | 0.000 | 0.000 | 0.000 |
| Isopropyl N-(3-chlorophenyl) N-methylcarbamate (8 lb./acre-in.) S-Ethyl N,N-di-n-propylthiolcarbamate (1.6 lb./acre-in.) | 0.000 | 0.000 | 0.000 | 0.000 | 0.000 | 0.000 | 0.000 | 0.000 |
| Isopropyl N-(3-chlorophenyl) N-methylcarbamate (8 lb./acre-in.) S-m-Propyl N-ethyl-N-n-butylthiolcarbamate (1.6 lb./acre-in.) | 0.000 | 0.000 | 0.000 | 0.000 | 0.000 | 0.000 | 0.000 | 0.000 |

| | 32 | 36 | 40 | 43 | 47 | 50 | 54 | 57 |
|---|---|---|---|---|---|---|---|---|
| Control | 0.080 | 0.075 | 0.089 | 0.120 | 0.075 | 0.060 | 0.110 | 0.115 |
| Isopropyl N-(3-chlorophenyl) N-methylcarbamate (8 lb./acre-in.) | 0.078 | 0.089 | 0.080 | 0.115 | 0.090 | | | |
| Isopropyl N-(3-chlorophenyl) N-methylcarbamate (8 lb./acre-in.) 4-Chlorophenyl N-methylcarbamate (1.6 lb./acre-in.) | 0.000 | 0.000 | 0.000 | 0.000 | 0.000 | 0.000 | 0.000 | 0.000 |
| Isopropyl N-(3-chlorophenyl) N-methylcarbamate (8 lb./acre-in.) 3-Chlorophenyl N-methylcarbamate (1.6 lb./acre-in.) | 0.000 | 0.000 | 0.000 | 0.000 | 0.007 | 0.008 | 0.007 | 0.012 |
| Isopropyl N-(3-chlorophenyl) N-methylcarbamate (8 lb./acre-in.) 2,4-Dichlorophenyl N-methylcarbamate (1.6 lb./acre-in.) | 0.002 | 0.000 | 0.032 | 0.060 | 0.105 | 0.088 | | |
| Isopropyl N-(3-chlorophenyl) N-methylcarbamate (8 lb./acre-in.) 2,4-Dinitro-6-sec-butylphenyl N-methylcarbamate (1.6 lb./acre-in.) | 0.047 | 0.115 | 0.115 | 0.120 | | | | |
| Isopropyl N-(3-chlorophenyl) N-methylcarbamate (8 lb./acre-in.) S-m-Propyl N,N-di-n-propylthiolcarbamate (1.6 lb./acre-in.) | 0.000 | 0.002 | 0.040 | 0.106 | 0.090 | | | |
| Isopropyl N-(3-chlorophenyl) N-methylcarbamate (8 lb./acre-in.) S-Ethyl N,N-di-n-propylthiolcarbamate (1.6 lb./acre-in.) | 0.000 | 0.095 | 0.092 | 0.080 | 0.081 | | | |
| Isopropyl N-(3-chlorophenyl) N-methylcarbamate (8 lb./acre-in.) S-m-Propyl N-ethyl-N-n-butylthiolcarbamate (1.6 lb./acre-in.) | 0.000 | 0.002 | 0.065 | 0.120 | 0.094 | | | |

| | 61 | 68 | 71 | 75 | 78 | 82 | 85 | 90 |
|---|---|---|---|---|---|---|---|---|
| Control | 0.095 | 0.075 | 0.090 | 0.105 | 0.085 | 0.060 | 0.065 | 0.095 |
| Isopropyl N-(3-chlorophenyl) N-methylcarbamate (8 lb./acre-in.) | | | | | | | | |
| Isopropyl N-(3-chlorophenyl) N-methylcarbamate (8 lb./acre-in.) 4-Chlorophenyl N-methylcarbamate (1.6 lb./acre-in.) | 0.007 | 0.000 | 0.005 | 0.005 | 0.013 | 0.040 | 0.025 | 0.075 |
| Isopropyl N-(3-chlorophenyl) N-methylcarbamate (8 lb./acre-in.) 3-Chlorophenyl N-methylcarbamate (1.6 lb./acre-in.) | 0.035 | 0.080 | 0.093 | 0.080 | | | | |
| Isopropyl N-(3-chlorophenyl) N-methylcarbamate (8 lb./acre-in.) 2,4-Dichlorophenyl N-methylcarbamate (1.6 lb./acre-in.) | | | | | | | | |
| Isopropyl N-(3-chlorophenyl) N-methylcarbamate (8 lb./acre-in.) 2,4-Dinitro-6-sec-butylphenyl N-methylcarbamate (1.6 lb./acre-in.) | | | | | | | | |
| Isopropyl N-(3-chlorophenyl) N-methylcarbamate (8 lb./acre-in.) S-m-propyl N,N-di-n-propylthiolcarbamate (1.6 lb./acre-in.) | | | | | | | | |
| Isopropyl N-(3-chlorophenyl) N-methylcarbamate (8 lb./acre-in.) | | | | | | | | |

TABLE 3-continued

| | GRAMS OF RYE GRASS TOP GROWTH PLANTED ON VARIOUS DAYS AFTER TREATMENT | | | | | | | |
|---|---|---|---|---|---|---|---|---|
| | NUMBER OF DAYS | | | | | | | |
| TEST COMPOUND | 61 | 68 | 71 | 75 | 78 | 82 | 85 | 90 |
| S-Ethyl N,N-di-n-propylthiolcarbamate (1.6 lb./acre-in.) | | | | | | | | |
| Isopropyl N-(3-chlorophenyl) N-methylcarbamate (8 lb./acre-in.) | | | | | | | | |
| S-n-Propyl N-ethyl-N-n-butylthiolcarbamate (1.6 lb./acre-in.) | | | | | | | | |

EXAMPLE IV

The procedure of Example II is followed to evaluate the herbicidal effectiveness of several of the test compounds. The results are shown in Table 4.

TABLE 4

| | GRAMS OF RYE GRASS TOP GROWTH PLANTED ON VARIOUS DAYS AFTER TREATMENT | | | |
|---|---|---|---|---|
| | NUMBER OF DAYS | | | |
| TEST COMPOUND | 1 | 5 | 8 | 12 |
| Control | 0.088 | 0.065 | 0.090 | 0.070 |
| 4-Chlorophenyl N-methylcarbamate (2 lb./acre-in.) | 0.082 | 0.065 | 0.090 | 0.110 |
| 3-Chlorophenyl N-methylcarbamate (2 lb./acre-in.) | 0.088 | 0.080 | 0.110 | 0.115 |

EXAMPLES V –VIII

For each phenyl N-alkylcarbamate being tested, three 500 gram soil samples are taken from a stock of Ohio loam soil. The equivalent of 8 pounds isopropyl N-phenylcarbamate per acre-inch of soil (0.0104 grams) is incorporated into two of the soil samples. Into one of the samples treated with isopropyl N-phenylcarbamate is additionally incorporated the equivalent of 2 pounds per acre-inch of soil (0.0026 grams) of the phenyl N-alkylcarbamate. Each of the carbamates is applied to the soil by atomizing the required volume of a dilute aqueous preparation of the carbamate onto the soil sample. Each treated sample is well mixed to thoroughly distribute the carbamates throughout the sample. The soil samples are stored in plastic bags at room temperature.

Periodically, 50 gram samples are taken from each of the stored soil samples. The 50 gram samples are placed in 6 ounce paper cups. Ten (10) rye grass seeds are planted in each cup. The cups are then sealed with cellophane held in place by rubber bands to maintain the moisture content of the soil. The cups are stored at room temperature near a window. Seven days from planting (considering the day of treatment to be the first day), the blades of rye grass are cut off at the soil line and weighed. The test compounds are:

Example V — 4-dimethylamino-3,5-dimethylphenyl N-methylcarbamate
Example VI — 2-isopropoxyphenyl N-methylcarbamate
Example VII — 4-dimethylamino-3-tolyl N-methylcarbamate
Example VIII — phenyl N-methylcarbamate In each instance, the weight of the top growth collected from the treated soil samples is compared with the weight of the top growth from the untreated control. In each Example, a significant difference in weights is found for a longer period between the control and the soil sample treated with both isopropyl N-phenylcarbamate and the phenyl N-alkylcarbamate than between the control and the soil sample treated only with isopropyl N-phenylcarbamate.

The extension of the soil persistence of isopropyl N-(3-chlorophenyl)carbamate by the phenyl N-alkylcarbamates of this invention is illustrated by the following examples.

EXAMPLE IX

Three (3) 500 gram soil samples are taken from a stock of Ohio loam soil. The equivalent of ten (10) pounds isopropyl N-(3-chlorophenyl)carbamate per acre-inch of soil (0.0132 grams) is incorporated into two of the soil samples. Into one of the samples treated with isopropyl N-(3-chlorophenyl)carbamate is additionally incorporated the equivalent of 2 pounds per acre-inch of soil (0.0026 grams) phenyl N-methylcarbamate. Each of the carbamates is applied to the soil by atomizing the required volume of a dilute aqueous preparation of the carbamate onto the soil sample. Each treated sample is well mixed to thoroughly distribute the carbamates throughout the sample. The soil samples are stored in plastic bags at room temperature.

Periodically, 50 gram samples are taken from each of the stored soil samples. The 50 gram samples are placed in 6 ounce paper cups. Ten (10) rye grass seeds are planted in each cup. The cups are then sealed with cellophane held in place by rubber bands to maintain the moisture content of the soil. The cups are stored at room temperature near a window. Seven days from planting (considering the day of planting to be the first day), the blades of rye grass are cut off at the soil line and weighed. Results are reported in Table 5.

TABLE 5

Weight in Grams of Top Growth of Rye Grass Seeds Planted at Intervals After Treatment of The Soil with Isopropyl N-(3-chlorophenyl)-Carbamate With and Without Phenyl N-methylcarbamate

| Days From Treatment | 5 | 11 | 19 | 25 |
|---|---|---|---|---|
| Control | 0.082 | 0.106 | 0.045 | 0.125 |
| 10 pounds per acre-inch isopropyl N-(3-chlorophenyl)carbamate | 0.041 | 0.097 | 0.075 | — |
| 10 pounds per acre-inch isopropyl N-(3-chlorophenyl)carbamate plus 2 pounds per acre-inch phenyl N-methylcarbamate | 0.000 | 0.000 | 0.020 | 0.067 |

In other tests, phenyl N-methylcarbamate is found to possess no significant herbicidal activity.

EXAMPLE X

From a stock of muck soil with high organic content are taken three 50 gram samples. Each of these samples is placed in a separate 1,000 milliliter flask. An aqueous suspension is prepared containing 150 ppm by weight isopropyl N-(3-chlorophenyl)carbamate. Three hundred (300) milliliters of this suspension is added to one of the flasks. Another 300 milliliter portion of the suspension is treated in one of the remaining flasks by the addition of 2 ppm phenyl N-methylcarbamate. Three hundred (300) milliliters of water is added to the third or control flask. Each flask is fitted with a two-hole stopper. An air line is connected to tubes extending through each stopper to contact the soil slurry in each flask. The remaining hole of each stopper openly communicates with the atmosphere. Air is constantly bubbled through the soil slurries to provide oxygen thereto. At selected intervals, 15 cc samples are taken from each flask and placed in petri dishes. Twenty cucumber seeds are placed on filter paper in each petri dish. The petri dishes are placed in a dark oven maintained at 30° C. After 4 days of germination, the lengths of the roots of the germinated seeds are measured. The average length of the roots is reported in Table 6.

TABLE 6

Average Length in Millimeters of Roots of Cucumber Seeds Germinated for Four Days in Contact With Aqueous Media Taken From Soil Slurries at Intervals After Treatment With Formulations of Isopropyl N-(3-chlorophenyl)carbamate

| Days After Treatment | 2 | 6 | 9 | 12 | 16 |
|---|---|---|---|---|---|
| Control | 55 | 55 | 40 | 40 | 42 |
| Isopropyl N-(3-chlorophenyl)-carbamate (150 ppm) | 8 | 10 | 36 | 73 | 56 |
| Isopropyl N-(3-chlorophenyl)-carbamate (150 ppm) plus phenyl N-methylcarbamate (2 ppm) | 7 | 10 | 9 | 8 | 9 |

EXAMPLES XI – XXI

The procedure of Examples V - VIII is repeated substituting isopropyl N-(3-chlorophenyl)carbamate for isopropyl N-phenylcarbamate and using the following phenyl N-alkylcarbamates:

Example XI — 2-isopropylphenyl N-methylcarbamate

Example XII — 2-isopropoxyphenyl N-methylcarbamate

Example XIII — 4-dimethylamino-3-tolyl N-methylcarbamate

Example XIV — 4-dimethylamino-3,5-xylyl N-methylcarbamate

Example XV — 4-chlorophenyl N-methylcarbamate

Example XVI — 3-chlorophenyl N-methylcarbamate

Example XVII — 2-chlorophenyl N-methylcarbamate

Example XVIII — 4-methylphenyl N-methylcarbamate

Example XIX — 3-methylphenyl N-methylcarbamate

Example XX — 2-methylphenyl N-methylcarbamate

Example XXI — 4-dimethylamino-3,5-dimethylphenyl-N-methylcarbamate

In each instance, the weight of the top growth collected from the treated soil samples is compared with the weight of the top growth collected from the untreated control. In each Example, a significant difference in weights is found for a longer period between the control and the soil sample treated with both isopropyl N-(3-chlorophenyl)-carbamate and the phenyl N-alkylcarbamate than between the control and the soil sample treated only with isopropyl N-(3-chlorophenyl)carbamate.

Although isopropyl N-phenylcarbamate may be formulated with the phenyl N-alkylcarbamates of this invention in a variety of fluid and solid formulations, the preferred formulation is a "flowable composition", i.e., a wettable powder in a wet or liquid state. According to this invention, it has been found that a highly satisfactory formulation may be produced by including in an aqueous medium between about 10 and about 60 percent by weight isopropyl N-phenylcarbamate and between about 1 and about 40 percent of the phenyl N-alkylcarbamate, based on the total weight of the formulation.

The density of the aqueous phase should be increased by the addition of a water soluble substance to substantially decrease the tendency of the solids to settle out of suspension. Usually, between ½ and 2 times the amount of water soluble substance required to adjust the density of the aqueous phase to that of isopropyl N-phenylcarbamate is included in the formulation. This amount is typically between about 5 and about 15 percent by weight of the formulation. A wide variety of water soluble substances is employable for this purpose. Hygroscopic inorganic salts with high water solubility, preferably above about 100 grams per liter at 25° C., are particularly useful. The hygroscopic water soluble inorganic salts of the alkali metals (including ammonium) and alkaline earth metals are preferred. Calcium chloride is an especially useful salt. Sodium sulfate and potassium chloride are further examples of useful salts.

A small amount, typically between about ¼ and about 5, usually between about 1 and about 2 percent by weight of a suitable dispersing agent or surfactant greatly enhances the stability of the flowable composition. It is further often desirable to include in the formulation a small amount, e.g., about 1/10 to about 1 percent by weight of a suitable anti-foaming agent. A plurality of suitable such additives are disclosed hereinafter.

The pH of the formulation may be adjusted if necessary. The usual values of pH fall in the range of from about 2 to about 10; more often they fall in the range of from about 5 to about 8. The pH of the formulation may be adjusted to the range pH 2–5, often about pH 3. When it is desired to acidify the formulation, the pH adjustment is conveniently accomplished by the addition of small amounts of acidic material (including acid salts). As a rule, the pH adjustment requires the addition of less than about 1 percent by weight of said acid or acid salt to the formulation. The mineral acids, e.g., HBr, HCl, $H_2SO_4$, $HNO_3$, $HClO_4$ or $H_3PO_4$ are useful. When it is desired to increase the pH of the formulation, small amounts of basic material (including basic salts) may be added. Sodium carbonate, potassium carbonate, sodium bicarbonate, potassium bicarbonate, trisodium phosphate, tripotassium phosphate, disodium hydrogen phosphate, dipotassium hydrogen phosphate, triammonium phosphate, sodium hydroxide and potassium hydroxide are useful for this purpose.

The following example describes the preparation of one of the novel formulations contemplated by this invention.

EXAMPLE XXII

To a ball mill of ½ gallon capacity are charged 167 milliliters of water, 0.8 gram phosphoric acid and 7.0 grams PB-92 (calcium lignosulfonate marketed by Lignosol Chemicals, Ltd., P.O. Box 2025, Quebec, Quebec, Canada). These ingredients are well mixed in the ball mill. Thirty-four (34) grams of calcium chloride are added to the mill and mixed until completely dissolved. Three-tenths (3/10) gram of "Surfynol" 104 ($R_1R_2C(OH)C \vdots CC(OH)R_1R_2$, m.p. 37° C., b.p. 260° C. ditertiary acetylenic glycol) is then added and mixed. One hundred seventy (170) grams of isopropyl N-phenylcarbamate and 20.0 grams of 4-chlorophenyl N-methylcarbamate are then added to the mill. The mixture is ground for about 5 hours until the desired particle size of about 10 microns is obtained. One gram of PB-92 and 0.1 gram of "Surfynol" 104 are then added to the mill. Grinding is continued for about 30 minutes. A formulation identical except for the deletion of the 4-chlorophenyl N-methylcarbamate is also prepared.

Ten (10) milliliters of each of the above formulations is separately diluted to 100 milliliters with water in two 100 milliliters graduates. Separate soil samples are treated with these diluted formulations in accordance with the procedure of Example V. The weight of the top growth collected from the treated soil samples is compared with the weight of the top growth from the untreated control. A significant difference in weights is found for a longer period between the control and the soil sample treated with both isopropyl N-phenylcarbamate and 4-chlorophenyl N-methylcarbamate than between the control and the soil sample treated only with isopropyl N-phenylcarbamate.

EXAMPLE XXIII

Sandy loam soil having (1) a mechanical analysis of 62 percent sand, 30 percent silt, and 8 percent clay, (2) an inherent organic matter level of 3.6 percent, and (3) a pH of 6.1 was modified by adding 2.0 percent by weight peat, 5.3 percent by weight dried cow manure, and sufficient lime to increase the pH to approximately 7.0. Portions of the modified soil were sprayed with solutions of test compounds. For each pound per acre reported in the results, 5.5 micrograms of test compound were applied to 1 gram of soil. The test compounds were then incorporated into their respective portions of soil by mechanical blenders. The treated portions of soil and untreated control soil were stored under moist conditions at room temperature. Aliquots of soil were removed from each portion of soil 1, 2, 4, and 8 weeks after treatment and placed in a 3 inch by 3 inch pot over a layer of untreated, sterilized soil. The depth of the treated soil in the pot was ¾ inch. Each pot was then seeded with test plants. After a growing period of approximately 4 weeks the herbicidal effectiveness of each test composition was evaluated and the results reported on a scale ranging from 0 (no injury) to 10 (all plants killed). The results are shown in Table 7. Abbreviations are:

| | |
|---|---|
| 4-CPMC | 4-Chlorophenyl N-methylcarbamate |
| CIPC | Isopropyl N-(3-chlorophenyl)carbamate |
| IPC | Isopropyl N-phenylcarbamate |
| QKGS | Quackgrass (Agropyron repens [L.] Beauv.) |
| WOAT | Wild Oats (Avena fatua L.) |
| BNGS | Barnyardgrass (Echinochloa crusgalli [L.] Beauv.) |
| CBGS | Crabgrass (Digitaria sanguinalis Scop.) |
| BKWT | Buckwheat (Polygonum convolvulus L.) |
| MNGY | Wild Morning Glory (mixture of Ipomoea purpurea Roth and Impomoea hederacea Jacq.) |

TABLE 7

PERSISTENCE OF SOIL-INCORPORATED HERBICIDE COMBINATIONS AS INFLUENCED BY 4-Chlorophenyl N-methylcarbamate

| Herbicide | Lb/A | Interval Weeks | QKGS | WOAT | BNGS | CBGS | BKWT | MNGY |
|---|---|---|---|---|---|---|---|---|
| 4-CPMC | 1 | 1 | 0 | 0 | 0 | 0 | 0 | 0 |
| CIPC | 4 | 1 | 10 | 10 | 8 | 2 | 10 | 8 |
| CIPC + 4-CPMC | 4 + 1 | 1 | 10 | 10 | 9 | 4 | 10 | 8 |
| IPC | 4 | 1 | 10 | 10 | 0 | 0 | 10 | 4 |
| IPC + 4-CPMC | 4 + 1 | 1 | 10 | 10 | 0 | 0 | 10 | 7 |
| 4-CPMC | 1 | 2 | 0 | 0 | 0 | 0 | 0 | 0 |
| CIPC | 4 | 2 | 10 | 10 | 8 | 4 | 10 | 8 |
| CIPC + 4-CPMC | 4 + 1 | 2 | 10 | 10 | 8 | 5 | 10 | 8 |
| IPC | 4 | 2 | 10 | 10 | 0 | 0 | 9 | 2 |
| IPC + 4-CPMC | 4 + 1 | 2 | 10 | 10 | 0 | 0 | 10 | 7 |
| 4-CPMC | 1 | 4 | 0 | 0 | 0 | 0 | 0 | 0 |
| CIPC | 4 | 4 | 5 | 5 | 3 | 3 | 9 | 4 |
| CIPC + 4-CPMC | 4 + 1 | 4 | 10 | 10 | 7 | 3 | 9 | 8 |
| IPC | 4 | 4 | 9 | 8 | 3 | 0 | 9 | 0 |
| IPC + 4-CPMC | 4 + 1 | 4 | 10 | 10 | 3 | 0 | 9 | 5 |
| 4-CPMC | 1 | 8 | 0 | 0 | 0 | 0 | 0 | 0 |
| CIPC | 4 | 8 | 0 | 1 | 0 | 0 | 8 | 1 |
| CIPC + 4-CPMC | 4 + 1 | 8 | 10 | 10 | 7 | 2 | 9 | 7 |
| IPC | 4 | 8 | 0 | 0 | 0 | 0 | 0 | 0 |
| IPC + 4-CPMC | 4 + 1 | 8 | 10 | 10 | 0 | 0 | 9 | 5 |

EXAMPLE XXIV

The procedure of Example XXIII was repeated. The results are shown in Table 8. Abbreviations are as stated in Example XXIII.

TABLE 8

PERSISTENCE OF SOIL-INCORPORATED HERBICIDE COMBINATIONS AS INFLUENCED BY 4-Chlorophenyl N-methylcarbamate

| Herbicide | Lb/A | Interval Weeks | QKGS | WOAT | BNGS | CBGS | BKWT | MNGY |
|---|---|---|---|---|---|---|---|---|
| 4-CPMC | 1 | 1 | 0 | 0 | 0 | 0 | 0 | 0 |
| CIPC | 4 | 1 | 9 | 9 | 0 | 0 | 8 | 0 |
| CIPC + 4-CPMC | 4 + 1 | 1 | 9 | 9 | 0 | 0 | 9 | 5 |
| IPC | 4 | 1 | 6 | 0 | 0 | 0 | 9 | 0 |
| IPC + 4-CPMC | 4 + 1 | 1 | 8 | 7 | 0 | 0 | 9 | 0 |
| 4-CPMC | 1 | 2 | 0 | 0 | 0 | 0 | 0 | 0 |
| CIPC | 4 | 2 | 5 | 0 | 0 | 0 | 7 | 0 |
| CIPC + 4-CPMC | 4 + 1 | 2 | 8 | 3 | 0 | 0 | 8 | 4 |
| IPC | 4 | 2 | 0 | 0 | 0 | 0 | 5 | 0 |
| IPC + 4-CPMC | 4 + 1 | 2 | 5 | 0 | 0 | 0 | 8 | 0 |
| 4-CPMC | 1 | 4 | 0 | 0 | 0 | 0 | 0 | 0 |
| CIPC | 4 | 4 | 0 | 0 | 0 | 0 | 7 | 0 |
| CIPC + 4-CPMC | 4 + 1 | 4 | 8 | 8 | 0 | 0 | 8 | 6 |
| IPC | 4 | 4 | 0 | 0 | 0 | 0 | 0 | 0 |
| IPC + 4-CPMC | 4 + 1 | 4 | 0 | 0 | 0 | 0 | 8 | 0 |
| 4-CPMC | 1 | 8 | 0 | 0 | 0 | 0 | 0 | 0 |
| CIPC | 4 | 8 | 0 | 0 | 0 | 0 | 0 | 0 |
| CIPC + 4-CPMC | 4 + 1 | 8 | 8 | 6 | 0 | 0 | 7 | 3 |
| IPC | 4 | 8 | 0 | 0 | 0 | 0 | 0 | 0 |
| IPC + 4-CPMC | 4 + 1 | 8 | 0 | 0 | 0 | 0 | 2 | 0 |

EXAMPLE XXV

In the late summer the soil in a field was prepared and was weed free. Various chemicals were sprayed on portions of the prepared soil as aqueous solutions. On about half the chemically treated soil area the chemicals were incorporated into the soil, whereas the chemicals on the remainder were left unincorporated. Portions of the incorporated area and unincorporated area as well as an untreated control plot were seeded with wheat and irrigated with approximately 2 acre-inches of water on the following day. Fourteen days after application of the test chemicals, the seeded portions were evaluated as approximate percent contol of wheat as compared with the untreated portion. Following this evaluation further portions of the treated and untreated areas were seeded with wheat, spray irrigated with approximately 2 acre-inches of water, and evaluated 14 days later. This procedure was repeated beginning 36, 48, and 63 days after application of the test chemicals. Subsequent seedings and evaluations were conducted at less frequent intervals. Approximately 15 days prior to each subsequent evaluation further portions of the treated and untreated areas were seeded with wheat and spray irrigated with approximately 2 acre-inches of water. These subsequent evaluations were made 124, 159, 212, and 273 days after application of test chemicals. The identity of the test chemicals, their rates of application, and the results are shown in Table 9.

TABLE 9

EFFECTIVENESS OF TEST COMPOSITIONS IN THE CONTROL OF WHEAT, EXPRESSED AS PER CENT OF UNTREATED CONTROL

| TEST COMPOSITION | DAYS AFTER APPLICATION OF TEST COMPOSITION | | | | | | | | |
|---|---|---|---|---|---|---|---|---|---|
| | 14 | 36 | 48 | 63 | 77 | 124 | 159 | 212 | 273 |
| UNINCORPORATED | | | | | | | | | |
| Isopropyl N-(3-chlorophenyl)carbamate (2 lb./acre) | 90 | 70 | 40 | 10 | 0 | 0 | 0 | 0 | 0 |
| Isopropyl N-(3-chlorophenyl)carbamate (2 lb./acre) and 4-Chlorophenyl N-methylcarbamate (0.7 lb./acre) | 100 | 90 | 70 | 50 | 50 | 30 | 20 | 0 | 20 |
| Isopropyl N-(3-chlorophenyl)carbamate (4 lb./acre) | 80 | 80 | 50 | 20 | 10 | 0 | 10 | 0 | 0 |
| Isopropyl N-(3-chlorophenyl)carbamate (4 lb./acre) and 4-Chlorophenyl N-methylcarbamate (1.4 lb./acre) | 100 | 100 | 100 | 100 | 100 | 80 | 50 | 50 | 10 |
| Untreated Control | Normal | Normal | Normal | Normal | Normal | Normal | Normal | Normal | Normal |
| INCORPORATED, 2 INCHES | | | | | | | | | |
| Isopropyl N-(3-chlorophenyl)carbamate (2 lb./acre) | 100 | 100 | 80 | 50 | 30 | 20 | 20 | 0 | 10 |
| Isopropyl N-(3-chlorophenyl)carbamate (2 lb,/acre) and 4-Chlorophenyl N-methylcarbamate (0.7 lb./acre) | 100 | 100 | 100 | 100 | 100 | 80 | 40 | 10 | 10 |
| Isopropyl N-(3-chlorophenyl)carbamate (4 lb./acre) | 100 | 100 | 90 | 30 | 20 | 20 | 10 | 10 | 0 |
| Isopropyl N-(3-chlorophenyl)carbamate (4 lb./acre) and 4-Chlorophenyl N-methylcarbamate (1.4 lb./acre) | 100 | 100 | 100 | 100 | 100 | 100 | 30 | 75 | 50 |
| Untreated Control | Normal | Normal | Normal | Normal | Normal | Normal | Normal | Normal | Normal |

EXAMPLE XXVI

Formulations of isopropyl N-(3-chlorophenyl)-carbamate, isopropyl N-phenylcarbamate, and 4-chlorophenyl N-methylcarbamate in various combinations were sprayed on the surface of quantities of unsterilized soil and immediately incorporated by mechanical blenders. The soil used was a sandy loam having: (1) a mechanical analysis of 60 percent sand, 34 percent silt, and 6 percent clay; (2) an organic matter content of 3.9 percent; and (3) a pH of 6.4. Treated soil and untreated soil were stored moist at room temperature in plastic boxes having dimensions of 7.5 inches by 3.5 inches by 10 inches. Each box contained approximately 6.5 pounds of soil. For each pound per acre of test compound reported in Table 10, the box contained 16.2 milligrams of test compound. Aliquots of soil were removed at 0, 2, 4, 6, and 8 weeks after chemical treatment and placed in pots in a layer about ¾ inch deep over untreated, sterilized soil. The pots were seeded with downy brome (*Bromus tectorum*, L.), moved to a greenhouse, and held three to four weeks. At the conclusion of the holding period the downy brome growth, if any, of each pot was inspected and given an injury rating which was based on a scale of 0 (no injury) to 10 (complete control) and which referred primarily to retardation. The identity of the test chemicals, their rates of application, and the results are shown in Table 10.

TABLE 10

PERSISTENCE OF PREEMERGENCE HERBICIDAL ACTIVITY
OF
VARIOUS CHEMICALS AGAINST DOWNY BROME AS
INFLUENCED BY
4-CHLOROPHENYL N-METHYLCARBAMATE

| NOMEN-CLATURE: | 4-CPMC | 4-Chlorophenyl N-methylcarbamate |
| | CIPC | Isopropyl N-(3-chlorophenyl)carbamate |
| | IPC | Isopropyl N-phenylcarbamate |

| Chemicals Applied | Lbs. per Acre | Rep. No. | Injury Rating for Plants Planted Indicated Number of Weeks After Chemical Treatment of Soil | | | | |
|---|---|---|---|---|---|---|---|
| | | | 0 | 2 | 4 | 6 | 8 |
| 4-CPMC | 2 | A | 0 | 0 | 0 | 0 | 0 |
| | | B | 0 | 0 | 0 | 0 | 0 |
| | | C | 0 | 0 | 0 | 0 | 0 |
| 4-CPMC | 1 | A | 0 | 0 | 0 | 0 | 0 |
| | | B | 0 | 0 | 0 | 0 | 0 |
| | | C | 0 | 0 | 0 | 0 | 0 |
| 4-CPMC | 0.5 | A | 0 | 0 | 0 | 0 | 0 |
| | | B | 0 | 0 | 0 | 0 | 0 |
| | | C | 0 | 0 | 0 | 0 | 0 |
| CIPC | 2 | A | 9 | 5 | 4 | 0 | 0 |
| | | B | 10 | 5 | 5 | 0 | 0 |
| | | C | 8 | 5 | 5 | 0 | 0 |
| CIPC | 4 | A | 10 | 10 | 10 | 0 | 0 |
| | | B | 10 | 10 | 10 | 0 | 0 |
| | | C | 10 | 10 | 10 | 0 | 0 |
| CIPC | 8 | A | 10 | 10 | 10 | 8 | 0 |
| | | B | 10 | 10 | 10 | 6 | 0 |
| | | C | 10 | 10 | 10 | 5 | 0 |
| CIPC + 4-CPMC | 2 + 0.5 | A | 10 | 8 | 9 | 10 | 5 |
| | | B | 10 | 8 | 9 | 10 | 5 |
| | | C | 10 | 9 | 9 | 10 | 5 |
| CIPC + 4-CPMC | 4 + 1 | A | 10 | 10 | 10 | 10 | 10 |
| | | B | 10 | 10 | 10 | 10 | 9 |
| | | C | 10 | 9 | 9 | 10 | 9 |
| CIPC + 4-CPMC | 8 + 2 | A | 10 | 10 | 10 | 10 | 10 |
| | | B | 10 | 10 | 10 | 10 | 10 |
| | | C | 10 | 10 | 10 | 10 | 10 |
| CIPC | 10 | A | 10 | 10 | 10 | 10 | 4 |
| | | B | 10 | 10 | 10 | 10 | 4 |
| | | C | 10 | 10 | 10 | 10 | 4 |

TABLE 10-continued

PERSISTENCE OF PREEMERGENCE HERBICIDAL ACTIVITY
OF
VARIOUS CHEMICALS AGAINST DOWNY BROME AS
INFLUENCED BY
4-CHLOROPHENYL N-METHYLCARBAMATE

| NOMEN-CLATURE: | 4-CPMC | 4-Chlorophenyl N-methylcarbamate |
| | CIPC | Isopropyl N-(3-chlorophenyl)carbamate |
| | IPC | Isopropyl N-phenylcarbamate |

| Chemicals Applied | Lbs. per Acre | Rep. No. | Injury Rating for Plants Planted Indicated Number of Weeks After Chemical Treatment of Soil | | | | |
|---|---|---|---|---|---|---|---|
| | | | 0 | 2 | 4 | 6 | 8 |
| CIPC | 5 | A | 10 | 10 | 10 | 10 | 0 |
| | | B | 10 | 10 | 10 | 10 | 0 |
| | | C | 10 | 10 | 10 | 10 | 0 |
| CIPC | 2.5 | A | 10 | 10 | 8 | 3 | 0 |
| | | B | 10 | 10 | 8 | 2 | 0 |
| | | C | 10 | 10 | 8 | 2 | 0 |
| IPC | 2 | A | 10 | 10 | 10 | 9 | 0 |
| | | B | 10 | 10 | 10 | 9 | 0 |
| | | C | 10 | 10 | 10 | 7 | 0 |
| IPC | 4 | A | 10 | 10 | 10 | 10 | 8 |
| | | B | 10 | 10 | 10 | 10 | 8 |
| | | C | 10 | 10 | 10 | 10 | 8 |
| IPC | 8 | A | 10 | 10 | 10 | 10 | 10 |
| | | B | 10 | 10 | 10 | 10 | 10 |
| | | C | 10 | 10 | 10 | 10 | 10 |
| IPC + 4-CPMC | 2 + 0.5 | A | 10 | 10 | 10 | 9 | 8 |
| | | B | 10 | 10 | 10 | 10 | 8 |
| | | C | 10 | 10 | 10 | 9 | 8 |
| IPC + 4-CPMC | 4 + 1 | A | 10 | 10 | 10 | 10 | 10 |
| | | B | 10 | 10 | 10 | 10 | 10 |
| | | C | 10 | 10 | 10 | 10 | 10 |
| IPC + 4-CPMC | 8 + 2 | A | 10 | 10 | 10 | 10 | 10 |
| | | B | 10 | 10 | 10 | 10 | 10 |
| | | C | 10 | 10 | 10 | 10 | 10 |
| IPC | 10 | A | 10 | 10 | 10 | 10 | 10 |
| | | B | 10 | 10 | 10 | 10 | 10 |
| | | C | 10 | 10 | 10 | 10 | 10 |
| IPC | 5 | A | 10 | 10 | 10 | 10 | 9 |
| | | B | 10 | 10 | 10 | 10 | 9 |
| | | C | 10 | 10 | 10 | 10 | 9 |
| IPC | 2.5 | A | 10 | 10 | 10 | 10 | 6 |
| | | B | 10 | 10 | 10 | 10 | 6 |
| | | C | 10 | 10 | 10 | 10 | 6 |

EXAMPLE XXVII

The procedure of Example II is followed to evaluate the soil lives of several test compositions. The identities of the test compounds, the rates of application, and the results are shown in Table 11.

TABLE 11

| TEST COMPOUND | GRAMS OF RYE GRASS TOP GROWTH PLANTED ON VARIOUS DAYS AFTER TREATMENT | | | | | | | |
|---|---|---|---|---|---|---|---|---|
| | NUMBER OF DAYS | | | | | | | |
| | 3 | 10 | 38 | 56 | 76 | 87 | 106 | 190 |
| Control | 0.114 | 0.120 | 0.102 | 0.103 | 0.089 | 0.078 | 0.065 | 0.079 |
| Isopropyl N-(3-chlorophenyl) N-methylcarbamate (4 lb/acre-in) | 0.000 | 0.000 | 0.032 | 0.043 | 0.087 | 0.076 | 0.094 | 0.074 |
| Isopropyl N-(3-chlorophenyl) N-methylcarbamate (4 lb/acre-in) 4-Chlorophenyl N-ethylcarbamate (1 lb/acre-in) | 0.000 | 0.000 | 0.000 | 0.000 | 0.008 | 0.009 | 0.054 | 0.066 |
| Isopropyl N-(3-chlorophenyl) N-methylcarbamate (4 lb/acre-in) 4-Chlorophenyl N,N-dimethylcarbamate (1 lb/acre-in) | 0.000 | 0.000 | 0.000 | 0.000 | 0.037 | 0.020 | 0.076 | 0.055 |
| Isopropyl N-(3-chlorophenyl) N-methylcarbamate (4 lb/acre-in) 4-Chlorophenyl N-methylcarbamate | 0.000 | 0.000 | 0.000 | 0.000 | 0.028 | 0.048 | 0.081 | 0.085 |

According to a particularly preferred embodiment of this invention, the herbicidal activity of isopropyl N-(3-chlorophenyl)carbamate against several common weeds is enhanced. Notable among these weeds are pigweed (Amaranthus L.), particularly redroot pigweed (*Amaranthus retroflexus* L.), ragweed (Ambrosia L.), wild oat (*Avena fatua* L.), morning glory (Ipomoea L.), mustard, particularly wild mustard (*Brassica kaber* D.C.), pinnatifida (Stokes), flax (Linum L.), crab grass (Digitaria Heist), johnsongrass (*Sorghum halepense* [L.] pers.), lambsquarter (Chenopodium L.), barnyardgrass (Echinochloa Beauv.) and foxtail (Setaria Beauv.), particularly yellow foxtail (*Setaria glauca* [L.] Beauv.). These weeds have generally evidenced high resistance to isopropyl N-(3-chlorophenyl)carbamate applied at customery rates, e.g., about 2 to about 8 pounds per acre. The presence of as little as about 5 percent by weight, based on the weight of the isopropyl N-(3-chlorophenyl)carbamate, of a phenyl N-alkylcarbamate, e.g., 4-chlorophenyl N-methylcarbamate, in the soil or formulation with the isopropyl N-(3-chlorophenyl)-carbamate substantially increases the effectiveness of isopropyl N-(3-chlorophenyl)carbamate to control these weeds. This increased effectiveness is accomplished without significantly increasing the susceptibility of crop plants such as cotton, grass seed, soybean, onion, vegetable crops, e.g., peas, beans, radishes, kidney beans, squash, potato and tomato and grain crops such as corn, wheat, barley and rice, to isopropyl N-(3-chlorophenyl)carbamate. Although the aforedescribed herbicidal effectiveness of isopropyl N-(3-chlorophenyl)carbamate is enhanced by the presence of even large excesses, e.g., 500 percent or more by weight, of the phenyl N-alkylcarbamate, useful quantities for field application typically range from about 10 to about 100, preferably about 20 to about 50 percent by weight, based on the isopropyl N-(3-chlorophenyl)carbamate.

The herbicidal compositions of the present invention may be formulated in several ways. Convenient formulations include clay granular formulations, wettable powders and emulsifiable concentrates. These formulations may be prepared in accordance with techniques well known to the art, particularly the techniques and practices presently employed in the production of commercial formulations of isopropyl N-(3-chlorophenyl)-carbamate. Examples of suitable formulations may be found in U.S. Pat. No. 2,695,225, the disclosure of which is hereby incorporated by reference. By following the teachings of that patent and substituting one or more of the phenyl N-alkylcarbamates disclosed herein for a portion of the isopropyl N-(3-chlorophenyl)carbamate, suitable formulations for the practice of the present invention are obtained.

Granular formulations may be prepared by spraying molten mixtures of isopropyl N-(3-chlorophenyl)carbamate and the phenyl N-alkylcarbamate directly onto an inert carrier. Suitable materials for granules include clays such as attapulgite clay or other materials resistant to physical deterioration by water. Examples of such materials include corn cobs, walnut shells, natural manures, wood flour, sawdust, wood shavings and plant stems or leaves. One good method of application of the molten carbamate mixture is to spray it on the granular carrier while agitating the granules in a rotary blender. Suitable granular formulations produced in this fashion contain, for example, from about 1 to about 30 percent by weight alkyl N-phenylcarbamate and from 1 to about 30 percent phenyl N-alkylcarbamate, the remainder, i.e., about 40 to about 98 percent by weight of the granules comprising inert material. An example of a preferred formulation is 20 percent by weight isopropyl N-(3-chlorophenyl)carbamate, 5 percent by weight phenyl N-methylcarbamate and 75 percent by weight attapulgite clay.

Another good formulation contains 10 percent by weight isopropyl N-(3-chlorophenyl)carbamate, 10 percent by weight isopropyl N-(3,4-dichlorophenyl)-carbamate, 5 percent by weight 4-chlorophenyl N-methylcarbamate and 75 percent by weight attapulgite clay.

Suitable wettable powders typically contain between about 5 and about 50 percent by weight alkyl N-phenylcarbamate and between about 1 and about 20 percent by weight of the phenyl N-alkylcarbamate in admixture with an inert powder, e.g., silica, such as Hi-Sil 233 or like finely-divided solid, typically siliceous or clay materials. Any convenient amount of the inert diluent may be employed. Useful quantities range from about 10 to about 50 percent by weight. Small amounts of dispersing and/or wetting agents are usually included in the formulations. Useful amounts of these agents typically range from less than about 1 percent through about 5 percent, usually less than about 3 percent by weight of the formulation. The wettable powder is typically dispersed in water for application. A suitable wettable powder has the following approximate composition:

| | |
|---|---|
| Isopropyl N-(3-chlorophenyl)carbamate | 40% |
| Phenyl N-methylcarbamate | 10% |
| Sodium lignosulfonate | 3% |
| Sodium N-methyl-N-oleoyl taurate (wetting agent) | 3% |
| Hi-Sil 233 | 44% |

Emulsifiable concentrates are prepared by blending from about 5 to about 50 percent by weight alkyl N-phenylcarbamate and from about 1 to about 20 percent by weight of a phenyl N-alkylcarbamate with an organic solvent and an emulsifier. A typical such formulation is as follows:

| | |
|---|---|
| Isopropyl N-(3-chlorophenyl)carbamate | 48% |
| 4-Chlorophenyl N-methylcarbamate | 10% |
| Xylene | 34% |
| Polyoxyethylene derivatives (fatty glycerides) and blends with alkyl aryl sulfonates (Atlox 2083) | 8% |

Among the organic solvents which find use in emulsion formulations are xylene, kerosene, methyl isobutylketone and other water insoluble hydrocarbons, notably the carbonyl hydrocarbon solvents. Other useful solvents include the edible oils, e.g., corn oil, olive oil, codliver oil, safflower oil and the like. Any solvent inert to the carbamate and immiscible with water, at least in the presence of suitable surface active agents or emulsifiers, may be employed.

The formulations of the present invention frequently include small amounts of various surfactants such as wetting agents, emulsifiers and dispersants. Anionic surfactants are required for wettable powders, notably those typified by Example XXII of this disclosure. Emulsion formulations generally require blends of ionic and anionic surfactants.

Many hundreds of such surfactants are available as commercial products. Well-known dispersing agents which are useful in wettable powders include the lignin surfactants (ligno sulfonates) such as those described in U.S. Pat. No. 2,491,832 and the alkyaryl sulfonates.

The ligno sulfonates of most interest are the metallic, notably the sodium and calcium, sulfonate salts. Molecular weights of these materials normally range from about 1,000 to about 20,000. Another useful class of surfactants comprises the formaldehyde-naphthalene sulfonate condensates typified by those disclosed in U.S. Pat. No. 2,516,095. Other useful dispersing agents are found among the alkali metal derivatives of unsaturated and aromatic hydrocarbons, the alkali metal alcoholates of long chain alcohols and the anhydrous alkali metal soaps of higher fatty acids. Particularly suitable wetting agents for wettable powders are the taurates typified by sodium N-methyl-N-oleoyl taurate. Sodium alkyl naphthalene sulfonates and the oleic acid ester of sodium isethionate are also especially useful. The condensation products of alkylene oxides with phenols and organic acids, the polyalkylene derivatives of sorbitan esters, complex ether alcohols and mahogany soaps are examples of useful ionic surfactants. Other surface active agents of the same or similar physical properties are known to the art and can be employed in the formulations of this invention.

It is often desirable to include in a formulation which is to be mixed with water, a small amount, e.g., about 1/10 to about 1 percent by weight of a suitable anti-foaming agent. Useful anti-foaming agents include the ditertiary acetylenic glycols, such as those marketed under the tradename SURFYNOL by Air Reduction Chemical and Carbide Company, 150 East 42nd Street, New York 17, New York. Other compounds known to the art to function as anti-foaming agents may be employed if desired. Such compounds include 2-octonol, sulfonated oils, and silicones. Useful silicones are those of low moleculare weight, i.e., the silicone fluids or oils. Typical of these are the methyl and ethyl substituted silocanes, such as the dimethylsiloxanes.

It is within contemplation that the formulations of this invention include other active ingredients in addition to the aforedisclosed carbamates. It may be desirable, for example, to include other herbicides in the formulation to increase the spectrum of herbicidal activity of the formulation.

Although the invention has been described with particular reference to details of certain specific embodiments, it is not intended to limit the scope of the invention except to the extent those details are recited in the appended claims.

I claim:

1. A herbicidal composition containing as a herbicidal component isopropyl N-(3-chlorophenyl)carbamate in an amount sufficient to be herbicidally effective when applied to the soil, and further containing an amount of 4-chlorophenyl N-methylcarbamate sufficient to extend the soil life of said isopropyl N-(3-chlorophenyl)carbamate.

2. The herbicidal composition of claim 1 wherein the weight ratio of said isopropyl N-(3-chlorophenyl)carbamate and said 4-chlorophenyl N-methylcarbamate is between 1:1 and 10:1.

3. A herbicidal composition containing as a herbicidal component isopropyl N-phenylcarbamate in an amount sufficient to be herbicidally effective when applied to the soil, and further containing an amount of 4-chlorophenyl N-methylcarbamate sufficient to extend the soil life of said isopropyl N-phenylcarbamate.

4. The herbicidal composition of claim 3 wherein the weight ratio of said isopropyl N-phenylcarbamate and said 4-chlorophenyl N-methylcarbamate is between 1:1 and 10:1.

5. A method of controlling weeds comprising applying to the area in which weeds are living both a herbicidal amount of a compound selected from the group consisting of isopropyl N-(3-chlorophenyl)carbamate and isopropyl N-phenylcarbamate and an amount of 4-chlorophenyl N-methylcarbamate sufficient to extend the soil life of said compound.

6. The method of claim 5 wherein said compound is isopropyl N-(3-chlorophenyl)carbamate.

7. The method of claim 5 wherein said compound is isopropyl N-phenylcarbamate.

* * * * *